(12) United States Patent
Ouchi (10) Patent No.: US 6,656,191 B2
(45) Date of Patent: Dec. 2, 2003

(54) RETRIEVAL BASKET DEVICE FOR AN ENDOSCOPE

(75) Inventor: Teruo Ouchi, Saitama (JP)

(73) Assignee: Pentax Corporation, Tokyo (JP)

( * ) Notice: Subject to any disclaimer, the term of this patent is extended or adjusted under 35 U.S.C. 154(b) by 120 days.

(21) Appl. No.: 09/973,119

(22) Filed: Oct. 10, 2001

(65) Prior Publication Data

US 2002/0042617 A1 Apr. 11, 2002

(30) Foreign Application Priority Data

Oct. 11, 2000 (JP) ........................................ 2000-310262

(51) Int. Cl.[7] .............................................. A61B 17/24
(52) U.S. Cl. ....................................................... 606/113
(58) Field of Search ................................ 606/113, 108, 606/110, 114, 127, 200

(56) References Cited

U.S. PATENT DOCUMENTS

| | | | | |
|---|---|---|---|---|
| 4,347,846 A | * | 9/1982 | Dormia ........................ | 606/127 |
| 4,611,594 A | * | 9/1986 | Grayhack et al. ............ | 606/127 |
| 4,633,871 A | * | 1/1987 | Shinozuka ................... | 606/127 |
| 5,059,199 A | * | 10/1991 | Okada et al. ................ | 606/127 |
| 6,077,274 A | | 6/2000 | Ouchi et al. | |
| 6,152,932 A | * | 11/2000 | Ternstrom .................... | 606/114 |
| 6,280,451 B1 | * | 8/2001 | Bates et al. .................. | 606/127 |
| 6,348,056 B1 | * | 2/2002 | Bates et al. .................. | 606/114 |
| 6,350,266 B1 | * | 2/2002 | White et al. ................. | 606/114 |
| 6,443,972 B1 | * | 9/2002 | Bosma et al. ................ | 606/200 |

FOREIGN PATENT DOCUMENTS

JP 58142018 9/1983

* cited by examiner

Primary Examiner—Julian W. Woo
Assistant Examiner—Victor Nguyen
(74) Attorney, Agent, or Firm—Greenblum & Bernstein P.L.C.

(57) ABSTRACT

A retrieval basket device includes a flexible sheath, a control wire which is inserted in the flexible sheath to be movable therein along an axis of the flexible sheath, and a basket constructed from a plurality of resilient wires and connected to a distal end of the control wire, wherein advancing and retreating movements of the control wire in the flexible sheath cause the basket to project out of, and retract into, a distal end of the flexible sheath whereby the basket bulges and narrows, respectively. The plurality of resilient wires are positioned at non-uniform angular intervals as viewed from the axial direction of the control wire.

11 Claims, 7 Drawing Sheets

RETRIEVAL BASKET DEVICE FOR AN ENDOSCOPE

BACKGROUND OF THE INVENTION

1. Field of the Invention

The present invention relates to a retrieval basket device which is introduced into the body through a treatment tool insertion channel of an endoscope.

2. Description of the Related Art

A typical retrieval basket device for an endoscope is provided with a control wire and a basket which is connected to the distal end of the control wire. The control wire is inserted into a flexible sheath to be freely movable in the flexible sheath along an axial thereof. The flexible sheath is introduced into the body through a treatment tool insertion channel of an endoscope. The basket is made of a plurality of resilient metal wires. These metal wires bulge due to the resiliency thereof when the control wire is moved in a direction to make the metal wires project out (bulge) of the distal end of the flexible sheath, and the metal wires become narrow when the control wire is moved in the other direction to sheathe the metal wires in the distal end of the flexible sheath.

By using such a retrieval basket device, a gallstone lodged in a bile duct can be caught from the side of the duodenum and extracted from the bile duct.

Figure 6:
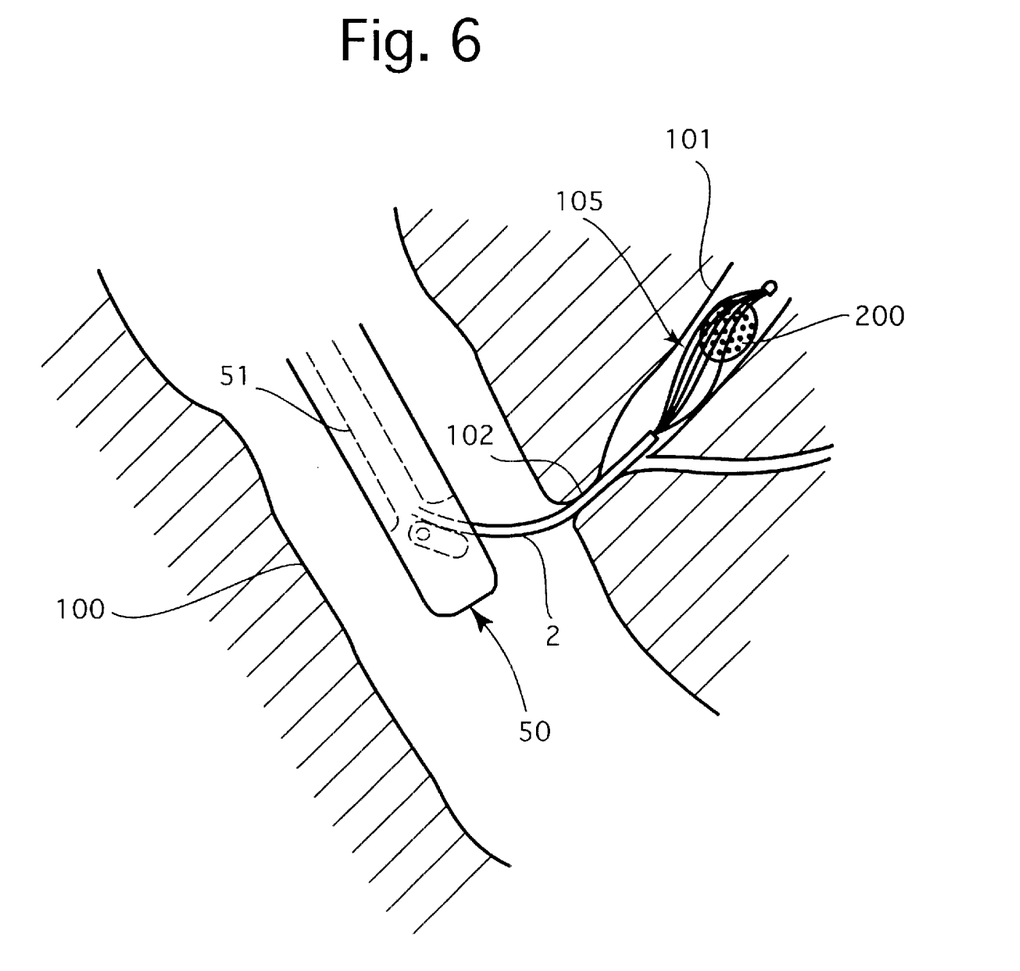
FIG. 6 is an explanatory diagram of an operational state of a conventional retrieval basket device.
Figure 7:
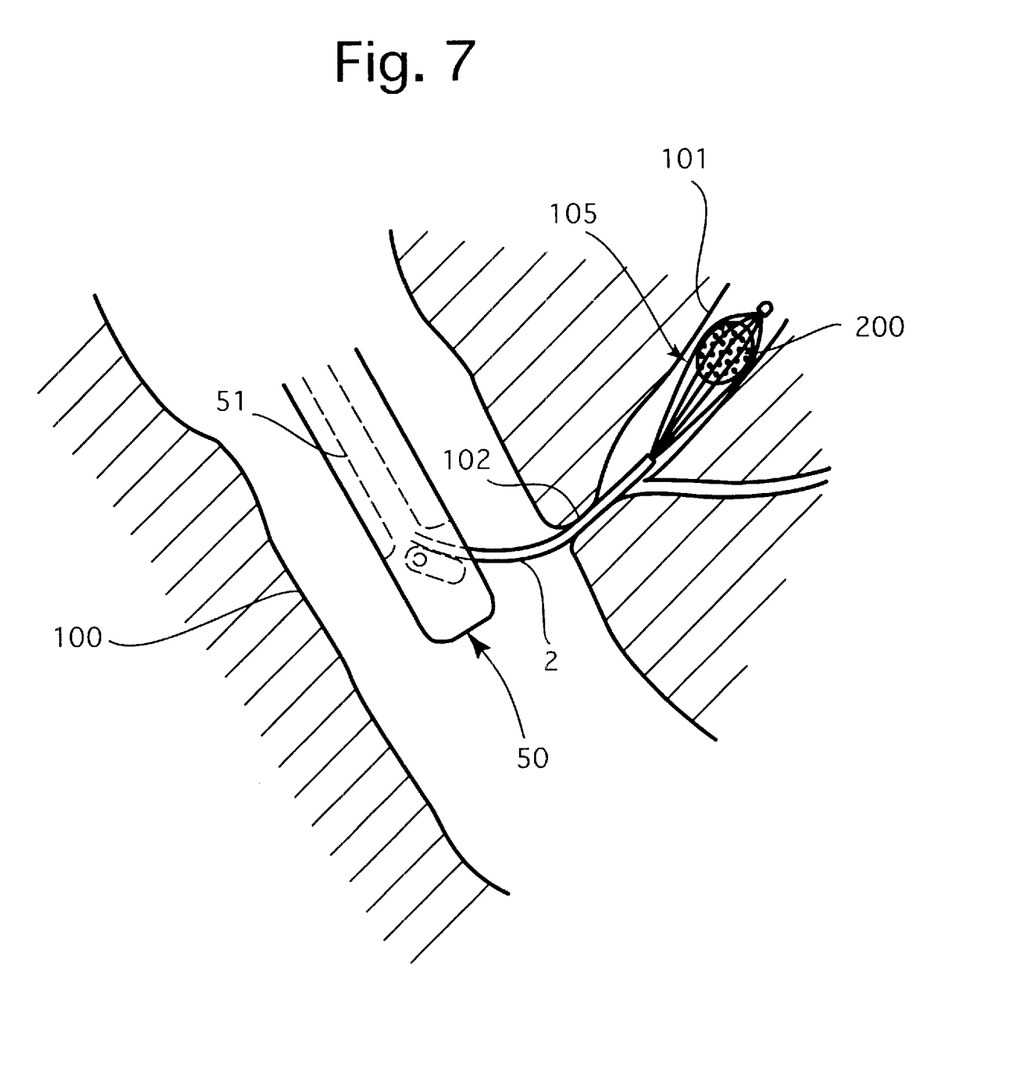
FIG. 7 is an explanatory diagram of another operational state of the conventional retrieval basket device shown in FIG. 6.

FIG. 6 shows a state where a basket 105 which projects out of the distal end of a flexible sheath 2 introduced into the duodenum 100 through a treatment tool insertion channel 51 provided in an insertion tube 50 of an endoscope. If a large gallstone 200 exits in a bile duct 101 as shown in FIG. 6, it is often the case that the gallstone 200 does not easily slip into the basket 105.

If the gallstone 200 captured in the basket 105 is too large to pass through an exit (Vater's papilla) 102 of the bile duct 101 which is constricted by a constrictor, there is a possibility that the gallstone 200 cannot be removed from the basket 105 and that the basket 105 be stuck in the bile duct 101.

SUMMARY OF THE INVENTION

An object of the present invention is to provide a retrieval basket device used for an endoscope which can easily catch large foreign matter and which can release the same easily as necessary.

To achieve the object mentioned above, according to an aspect of the present invention, a retrieval basket device is provided, including a flexible sheath, a control wire which is inserted in the flexible sheath to be movable therein along an axis of the flexible sheath, and a basket constructed from a plurality of resilient wires and connected to a distal end of the control wire, wherein advancing and retreating movements of the control wire in the flexible sheath cause the basket to project out of, and retract into, a distal end of the flexible sheath whereby the basket bulges and narrows, respectively. The plurality of resilient wires are positioned at non-uniform angular intervals as viewed from the axial direction of the control wire.

Preferably, the plurality of resilient wires are positioned so that a first angular interval between two adjacent resilient wires of the plurality of resilient wires is greater than a second angular interval between any other two adjacent resilient wires of the plurality of resilient wires.

In an embodiment, the first angular interval is equal to or greater than an angular interval which is double that of the second angular interval.

In an embodiment, an angular interval between the two adjacent resilient wires positioned at the first interval about an axis of the basket is in a range of approximately 60 through 90 degrees.

In an embodiment, each of the two adjacent resilient wires positioned at the first angular interval is more flexible than any other resilient wires of the plurality of resilient wires.

Preferably, the plurality of resilient wires bend at more than two points on each of the plurality of resilient wires to form the shape of the basket.

In an embodiment, all resilient wires of the plurality of resilient wires except the two adjacent resilient wires, positioned at the first interval, are arranged at approximately equal angular intervals.

The present disclosure relates to subject matter contained in Japanese Patent Application No. 2000-310262 (filed on Oct. 11, 2000) which is expressly incorporated herein by reference in its entirety.

BRIEF DESCRIPTION OF THE DRAWINGS

The present invention will be described below in detail with reference to the accompanying drawings in which.

DESCRIPTION OF THE PREFERRED EMBODIMENTS

Figure 1:
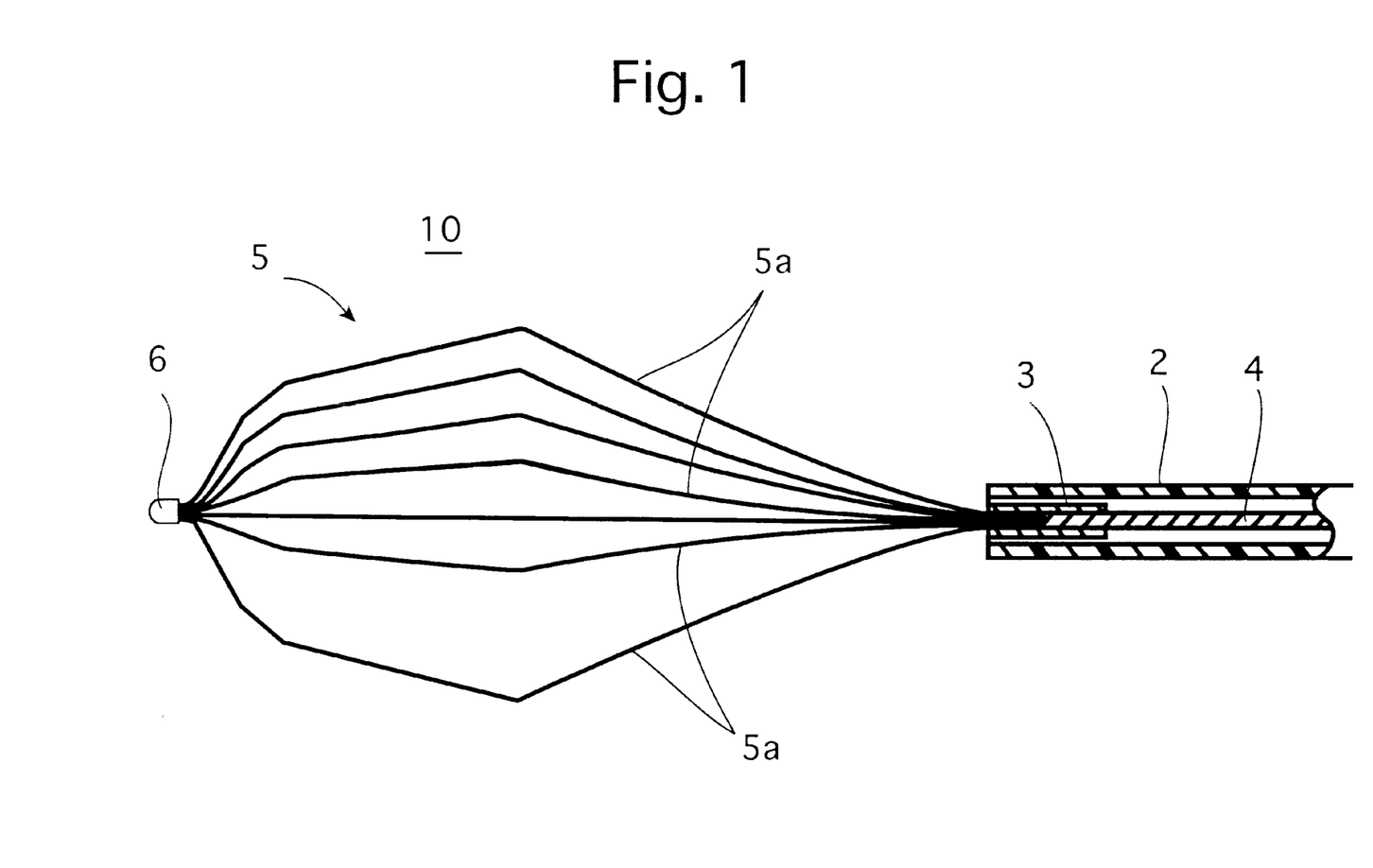
FIG. 1 is a side elevation, which is partly in cross section, of the distal end of the first embodiment of a retrieval basket device to which the present invention is applied.

FIG. 1 shows the distal end of the first embodiment of a retrieval basket device 10 to which the present invention is applied. The retrieval basket device 10 is utilized by being introduced into the body through a treatment tool insertion channel 51 provided in a flexible insertion tube 50 of an endoscope (see FIGS. 3 and 4).

The retrieval basket device 10 is provided with a flexible sheath 2. The flexible sheath 2 can be made of for example, a tetrafluoride ethylene resin, and the outer diameter and the length of the flexible sheath 2 are, for example, approximately two millimeters and approximately two meters, respectively. The retrieval basket device 10 is provided in the flexible sheath 2 with a control wire 4. The control wire 4 is movable (so as to advance and retreat) within the flexible sheath 2 along an axis thereof. The control wire 4 can be made of, for example, stainless strands.

The retrieval basket device 10 is provided at the distal end of the control wire 4 with a basket 5. The rear end of the basket 5 is fixed to the distal end of the control wire 4 via a connector pipe 3. The basket 5 is made of a plurality of resilient fine wires 5a which bend at more than two points on each wire 5a to collectively form the shape of a basket.

Each resilient fine wire 5a can be either a stainless solid wire or a stranded wire. The tips of the plurality of resilient fine wires 5a are tied (connected) at an end tip 6. In this particular embodiment, the number of the plurality of resilient fine wires 5a is ten as shown in FIG. 2, but is not limited solely to this particular number.

Advancing and retreating movements of the control wire 4 within the flexible sheath 2 via an operation of a control portion (not shown) of the retrieval basket device 10, which is connected to the proximal end (not shown) of the flexible sheath 2, cause the basket 5 to project out of and retract into the distal end of the flexible sheath 2, respectively.

The basket 5 bulges to form the shape of a basket due to the resiliency thereof when the control wire 4 is moved in a direction (to the left as viewed in FIG. 1) to make the basket 5 project out of the distal end of the flexible sheath 2. The basket 5 is forced to narrow against the resiliency thereof when the control wire 4 is moved in the other direction (to the right as viewed in FIG. 1) to sheathe the basket 5 in the distal end of the flexible sheath 2.

Figure 2:
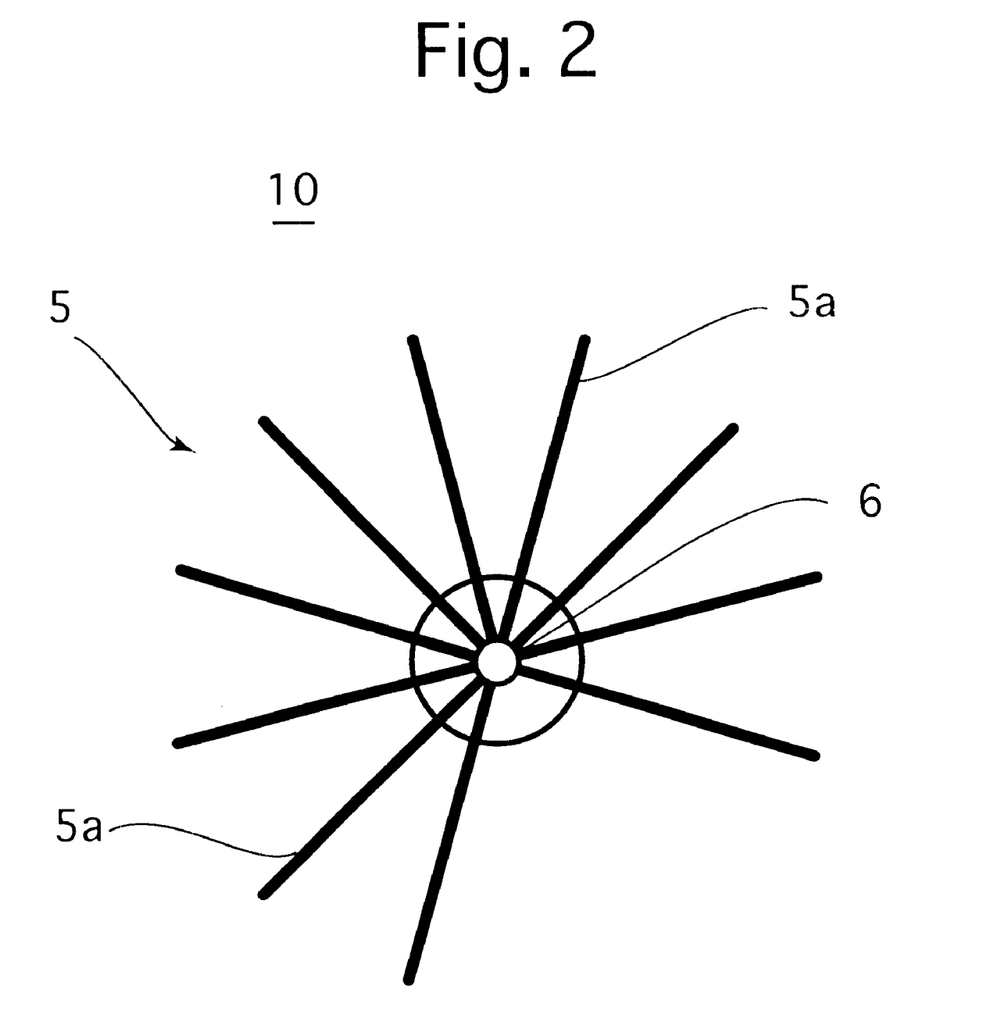
FIG. 2 is a front elevational view of the distal end of the retrieval basket device shown in FIG. 1.

As shown in FIG. 2, the resilient fine wires 5a are arranged at angular intervals of approximately 30 degrees about the axis of the basket 5, except for the angular interval between specific two adjacent resilient fine wires 5a which has an angular interval of approximately 90 degrees.

Figure 3:
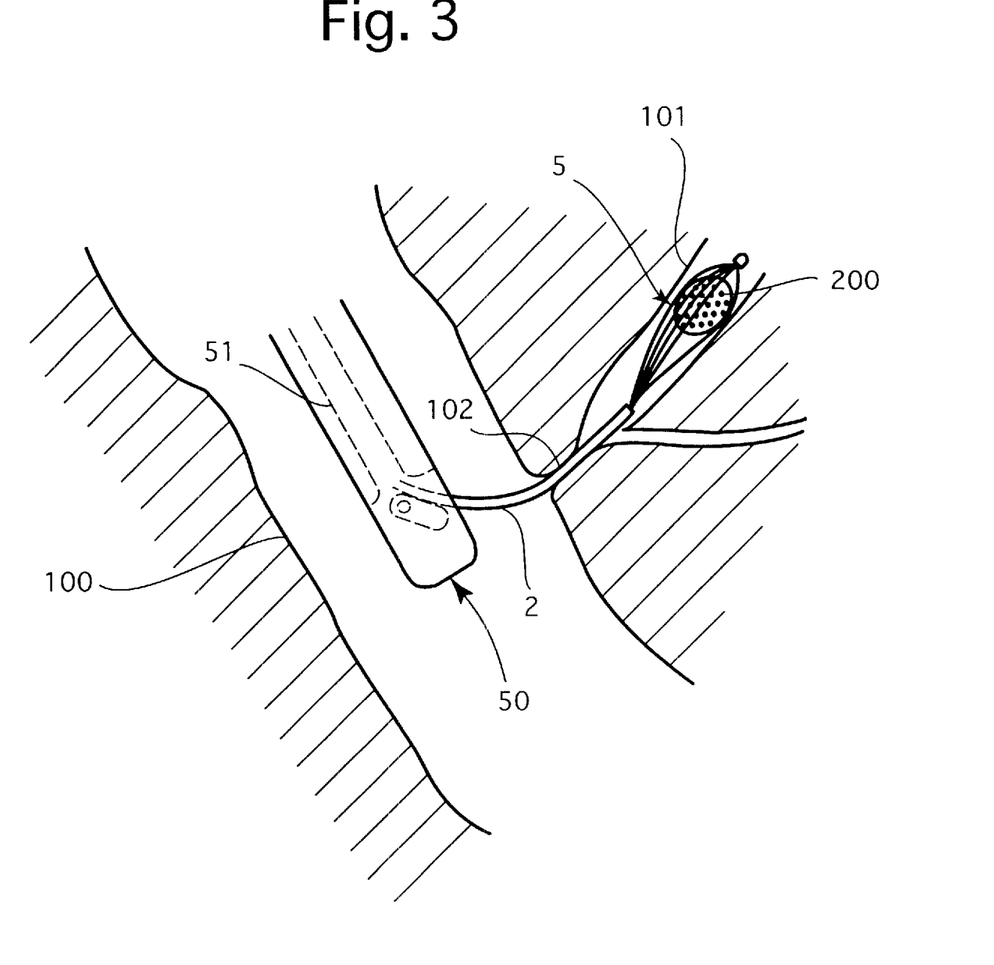
FIG. 3 is an explanatory diagram of an operational state of the retrieval basket device shown in FIG. 1.

FIG. 3 shows an operational state of retrieval basket device 10 according to the first embodiment. In this state, the retrieval basket device 10 is introduced into the body through the treatment tool insertion channel 51, and the distal end of the flexible sheath 2 is inserted into the bile duct 101 from the duodenum 100 via the exit 102 of the bile duct 101.

Since the angular interval between the above-mentioned specific two adjacent resilient fine wires 5a is greater than the angular interval between any other two adjacent resilient fine wires 5a, the gallstone 200 can enter the basket 5 if the basket 5 is moved back and forth in the axial direction thereof several times with the basket 5 remaining widely open.

Figure 4:
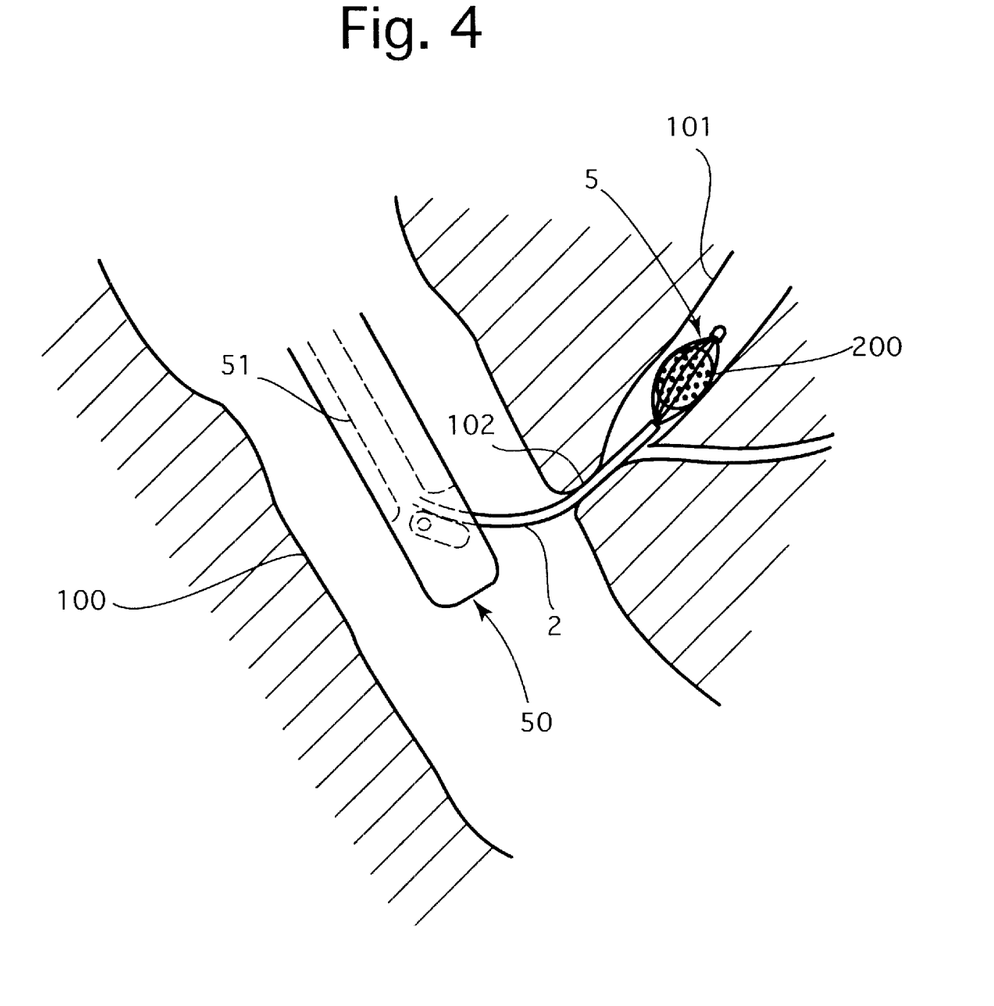
FIG. 4 is an explanatory diagram of another operational state of the retrieval basket device shown in FIG. 1.

Once the gallstone 200 enters the basket 5, the gallstone 200 is constricted and caught by the basket 5 as shown in FIG. 4 by pulling the control wire 4. Thereafter, the gallstone 200 is extracted from the body by pulling the flexible sheath 2.

If the gallstone 200 which is captured in the basket is too large to be extracted from the bile duct 101 to the duodenum 100, the gallstone 200 easily slips out of the basket 5 by inserting the control wire 4 to make the basket 5 bulge, i.e., to cause the basket 5 to return back to an open state shown in FIG. 3. Once the gallstone 200 slips out of the basket 5, the basket 5 can be pulled out of the bile duct 101. In this case, it is generally the case that a surgical operation in which the exit 102 of the bile duct 101 is cut to widen the exit 102 is performed.

Figure 5:
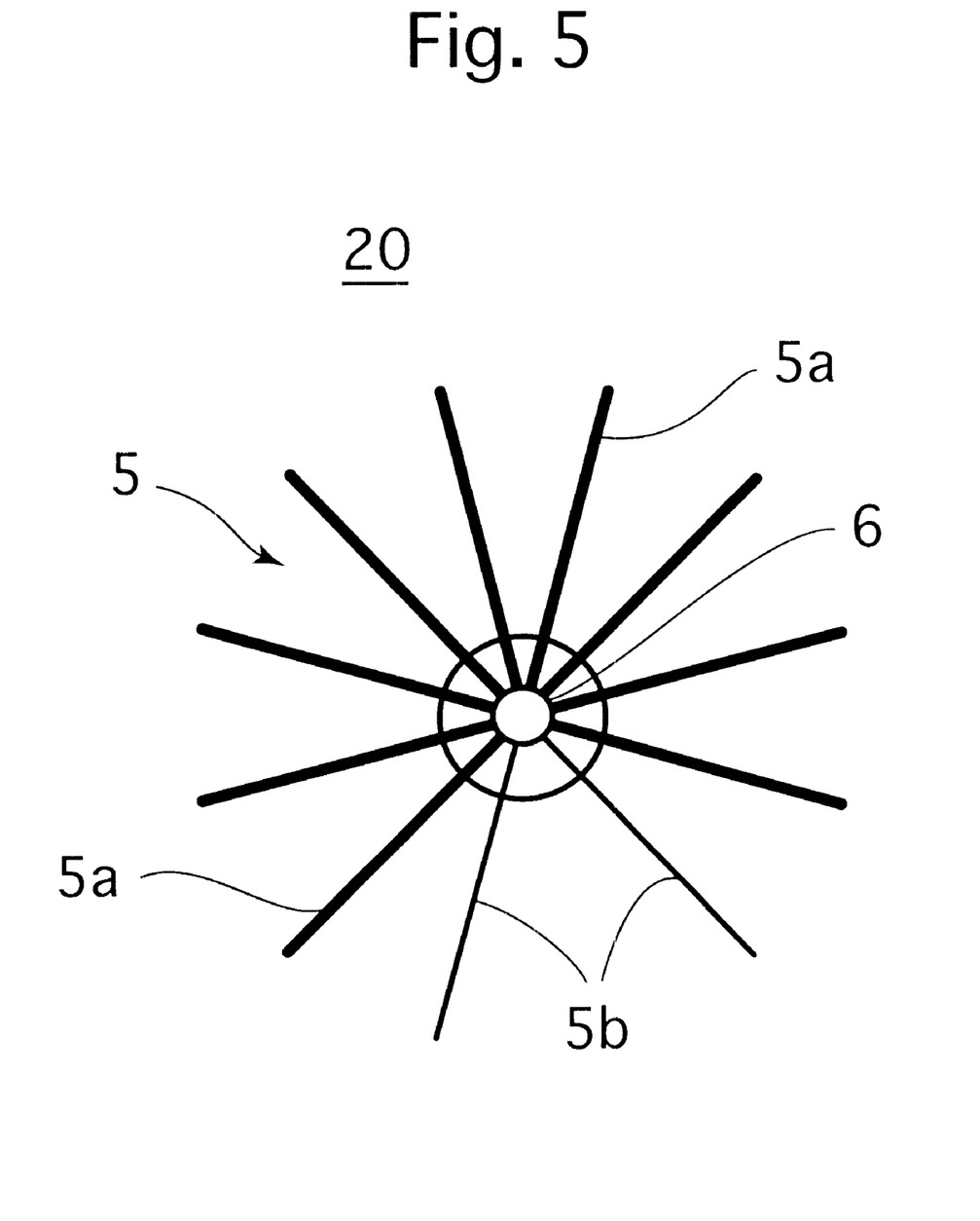
FIG. 5 is a view similar to that of FIG. 2, illustrating the second embodiment of the retrieval basket device to which the present invention is applied.

FIG. 5 is a front elevational view of the distal end of a retrieval basket device 20 according to the second embodiment, to which the present invention is applied. In this embodiment, the basket 5 is made of eleven resilient fine wires (5a and 5b) which bend at more than two points on each wire to form the shape of a basket. The eleven resilient fine wires include nine resilient fine wires 5a and two resilient fine wires 5b which are more flexible than the nine resilient fine wires 5a. The angular interval between the two resilient fine wires 5b is greater than the angular interval between any other two adjacent resilient fine wires 5a. The nine resilient fine wires 5a are arranged at approximately equal angular intervals.

The flexibility of each resilient fine wire 5a and the flexibility of each resilient fine wire 5b are determined relative to each other. Accordingly, for instance, a solid wire having a 0.15 mm diameter and a solid wire having a 0.05 mm diameter can be used as each resilient fine wire 5a and each resilient fine wire 5b, respectively, each resilient fine wire 5b being more flexible than each resilient fine wire 5a. Alternatively, a solid wire and a stranded wire which is more flexible than the solid wire can be used as each resilient fine wire 5a and each resilient fine wire 5b, respectively.

Alternatively, the number of wires which form a stranded wire used as each resilient fine wire 5a can be different from that used as each resilient fine wire 5b. For instance, a stranded wire consisting of three large-diameter wires and a stranded wire consisting of nineteen small-diameter wires can be used as each resilient fine wire 5a and each resilient fine wire 5b, respectively. Instead of this structure, the number of wires which form a stranded wire used as each resilient fine wire 5a can be identical to that used as each resilient fine wire 5b. In this case, the diameter of each wire of a stranded wire used as each resilient fine wire 5a only needs to be different from that used as each resilient fine wire 5b.

As can be understood from the above description, by providing the basket 5 with the two resilient fine wires 5b, which are more flexible than any other resilient fine wires 5a and the interval between which is smaller than the interval between any other two adjacent resilient fine wires 5a, the interval between the two resilient fine wires 5b widens easily by bringing the two resilient fine wires 5b into pressing contact with the gallstone 200. Therefore, even the large gallstone 200 can be easily caught and released. In the retrieval basket device 20 of the second embodiment, although the resiliency of each of the two resilient fine wires 5b may be small, the basket 5 bulges properly to form the shape of a basket due to sufficient resiliency of each of the other resilient fine wires 5a.

In the retrieval basket device 20 according to the second embodiment, the interval between the two resilient fine wires 5b is set at approximately 60 degrees. It is preferable that the interval between the two resilient fine wires 5b be at least approximately 60 degrees to catch a large gallstone. However, it is preferable that the interval between the two resilient fine wires 5b be equal to or smaller than approximately 90 degrees so that a gallstone caught in the basket 5 does not easily slip out of the basket 5.

In each of the first and second embodiments of the retrieval basket devices 10 and 20, if the angular interval between the two resilient fine wires 5b is equal to or greater than double the angular interval between any other two adjacent fine wires 5a, satisfactory results can be attained, i.e., large foreign matter can be caught by the basket 5 easily, and also can be released from the basket 5 easily if necessary.

In each of the first and second embodiments of the retrieval basket devices, the number of the resilient fine wires 5a is not limited solely to the above described embodiments, and the angular intervals at which the resilient fine wires 5a and 5b are arranged are not limited solely to the above described angular intervals. Furthermore, the shape of the basket 5 is not limited solely to the above illustrated particular shape.

As can be understood from the foregoing, according to a retrieval basket device to which the present invention is applied, since the interval between two adjacent resilient wires of a basket is greater than the interval between any other two adjacent resilient wires of the basket, even a large foreign matter can be caught by the basket easily, and also can be released from the basket easily if necessary. This ensures safety of the retrieval basket device.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A retrieval basket device comprising:

a flexible sheath;

a control wire which is inserted in said flexible sheath to be movable therein along an axis of said flexible sheath; and a basket constructed from a plurality of resilient wires and connected to a distal end of said control wire, wherein advancing and retreating movements of said control wire in said flexible sheath cause said basket to project out of, and retract into, a distal end of said flexible sheath whereby said basket bulges and narrows, respectively; said plurality of resilient wires being positioned at non-uniform angular intervals as viewed from the axial direction of said control wire, so that a first angular interval between two adjacent resilient wires of said plurality of resilient wires is greater than a second angular interval between any other two adjacent resilient wires of said plurality of resilient wires; wherein each of said two adjacent resilient wires positioned at said first angular interval is more flexible than any other resilient wires of said plurality of resilient wires.

2. The retrieval basket device according to claim 1, wherein said first angular interval is equal to or greater than an angular interval which is double said second angular interval.

3. The retrieval basket device according to claim 1, wherein said first angular interval is in a range of approximately 60 through 90 degrees.

4. The retrieval basket device according to claim 1, wherein said plurality of resilient wires bend at more than two points on each of said plurality of resilient wires to form the shape of said basket.

5. The retrieval basket device according to claim 1, wherein all resilient wires of said plurality of resilient wires, except said two adjacent resilient wires positioned at said first angular interval, are arranged at approximately equal angular intervals.

6. A retrieval basket device comprising:

a flexible sheath;

a control wire which is inserted in said flexible sheath to be movable therein along an axis of said flexible sheath; and a basket constructed from a plurality of resilient wires and connected to a distal end of said control wire, wherein advancing and retreating movements of said control wire in said flexible sheath cause said basket to project out of, and retract into, a distal end of said flexible sheath whereby said basket bulges and narrows, respectively, said plurality of resilient wires being connected to a common end tip portion spaced from the distal end of said control wire, said plurality of resilient wires being positioned at non-uniform angular intervals as viewed from the axial direction of said control wire, so that a first angular interval between two adjacent resilient wires of said plurality of resilient wires is greater than a second angular interval between any other two adjacent resilient wires of said plurality of resilient wires.

7. The retrieval basket device according to claim 6, wherein said first angular interval is equal to or greater than an angular interval which is double said second angular interval.

8. The retrieval basket device according to claim 6, wherein said first angular interval is in a range of approximately 60 through 90 degrees.

9. A The retrieval basket device according to claim 6, wherein each of said two adjacent resilient wires positioned at said first angular interval is more flexible than any other resilient wires of said plurality of resilient wires.

10. The retrieval basket device according to claim 6, wherein said plurality of resilient wires bend at more than two points on each of said plurality of resilient wires to form the shape of said basket.

11. The retrieval basket device according to claim 6, wherein all resilient wires of said plurality of resilient wires, except said two adjacent resilient wires positioned at said first angular interval, are arranged at approximately equal angular intervals.

* * * * *